US006280718B1

(12) United States Patent
Kaufman et al.

(10) Patent No.: US 6,280,718 B1
(45) Date of Patent: Aug. 28, 2001

(54) HEMATOPOIETIC DIFFERENTIATION OF HUMAN PLURIPOTENT EMBRYONIC STEM CELLS

(75) Inventors: Dan S. Kaufman; James A. Thomson, both of Madison, WI (US)

(73) Assignee: Wisconsin Alumni Reasearch Foundation, Madison, WI (US)

( * ) Notice: Subject to any disclaimer, the term of this patent is extended or adjusted under 35 U.S.C. 154(b) by 0 days.

(21) Appl. No.: 09/435,578

(22) Filed: Nov. 8, 1999

(51) Int. Cl.$^7$ .............................. C12N 5/00; C12N 15/00
(52) U.S. Cl. ..................... 424/93.1; 424/93.7; 435/325; 435/366; 435/375
(58) Field of Search ................... 424/93.1, 93.7; 435/325, 366, 375

(56) References Cited

U.S. PATENT DOCUMENTS 5,635,386 * 6/1997 Palsson et al. ..................... 435/372
5,843,780   12/1998 Thomson ............................ 435/363
5,914,268    6/1999 Keller et al. ....................... 435/325

FOREIGN PATENT DOCUMENTS

98/07841   2/1998  (WO) .

OTHER PUBLICATIONS

National Institutes of Health Guidelines for Research Using Human Pluripotent Stem Cells. National Institutes of Health, www.nih.gov/news/stemcell/stemcellguidelines.htm, pp. 1–13, Aug. 24, 2000.*
Bradley et al. Modifying the Mouse: Design and Desire. Bio/Technology, vol. 10, pp. 534–539, May 1992.*
Clark et al. Germ Line Manipulation: Applications in Agriculture and Biotechnology. Transgenic Animals. p. 250, 1992.*
Notarianni et al. Maintenance and Differentiation in Culture of Pluripotential Embryonic Cell Lines from Pig Blastocysts. J. Reprod. Fert., Suppl. 41, pp. 51–56, 1990.*
Seung, E. et al. Allogeneic hematopoietic chimerism in mice treated with sublethal myeloablation and anti–CD154 antibody. Blood 95:2175–2182, 2000.*
Thomson, J.A. & Odorico, J.S. Human embryonic stem cell and embryonic germ cell lines. Trends Biotechnol. 18:53–57, 2000.*
Gandy, K.L. & Weissman, I.L. Tolerance of allogeneic heart grafts in mice simultaneously reconstituted with purified allogeneic hematopoietic stem cells. Transplanatation 65:295–304, 1998.*
Klug, M.G. et al. Genetically selected cardiomyocytes from differentiating embryonic stem cells form stable intracardiac grafts. J. Clin. Invest. 98:216–224, 1996.*
Khanna, R. et al. Localization of Epstein–Barr virus cytotoxic T cell epitopes using recombinant vaccinia: Implications for vaccine development. J. Exp. Med. 176:169–176, 1992.*
F. Li et al., Hematopoietic Differentiation In Vitro Of Rhesus Monkey Embryonic Stem Cells, 92 Blood 368a (1998).
G. Keller, In Vitro Differentiation Of Embryonic Stem Cells, 7 Current Opinion In Cell Biology 862–869 (1995).
C. Baum et al., Isolation Of A Candidate Human Hematopoietic Stem–cell Population, 89 PNAS USA.2804–2808 (1992).
M. Weiss, Embryonic Stem Cells And Hematopoietic Stem Cell Biology, 11 Aplastic Anemia And Stem Cell Biology, 1185–1195 (1997).
S. Morrison et al., The Biology Of Hematopoietic Stem Cells, 11 Annu. Rev. Cell Dev. Biol., 35–71 (1995).
J. Thomson et al., Embryonic Stem Cell Lines Derived From Human Blastocysts, 282 Science 1145 et seq. (1998).
T. Nakano et al., Generation Of Lymphohematopoietic Cells From Embryonic Stem Cells In Culture, 265 Science 1098–1101 (1994).
F. Li et al., unpublished abstract dated before Aug. 30, 1999, Bone Morphogenetic Protein–4 Induces Efficient Hematopoietic Development Of Rhesus Monkey Embryonic Stem Cells In Vitro.

* cited by examiner

Primary Examiner—Jill D. Martin
(74) Attorney, Agent, or Firm—Quarles & Brady LLP

(57) ABSTRACT

Disclosed herein are methods of obtaining human hematopoietic cells from human pluripotent embryonic stem cells using mammalian stromal cells. Hematopoietic cells derived in this way are useful for creating cell cultures suitable for transplantation, transfusion, and other purposes.

10 Claims, No Drawings

HEMATOPOIETIC DIFFERENTIATION OF HUMAN PLURIPOTENT EMBRYONIC STEM CELLS

CROSS REFERENCES TO RELATED APPLICATIONS

Not applicable.

STATEMENT REGARDING FEDERALLY SPONSORED RESEARCH

BACKGROUND OF THE INVENTION

The present invention relates to the use of human embryonic stem cells to create blood-related cells, and the use of those blood-related cells for various purposes.

Techniques for isolating stable cultures of human embryonic stem cells have recently been described by our laboratory. See U.S. patent No. 5,843,780 and J. Thomson et al., 282 Science 1145–1147 (1998). The disclosure of these publications and of all other publications referred to herein are incorporated by reference as if fully set forth below.

We have deposited two of our human embryonic stem cell lines with the American Type Culture Collection, 10801 University Boulevard, Manassas, Va. 20110-2209 U.S.A. on Jul. 7, 1999 and Jul. 15, 1999 respectively. Taxonomic descriptions of these deposits are human embryonic stem cell lines H1 and H9 respectively. It has been proposed in these publications that such cell lines may be used for, among other things, providing a source of specified cell lines of various types for research, transplantation and other purposes.

Under the storage and culturing conditions described in these publications the cell lines are maintained long term without differentiation into specific cell types. When the cell lines are subsequently injected into immunodeficient mice, they form teratomas demonstrating differentiation into multiple tissue types.

When ES cells are used to produce desired cells, it is often preferable to optimize differentiation towards specific cell types. In the case of hematopoietic cells it is desirable that this result in hematopoietic cells that can be isolated and used to form multiple hematopoietic lineages. These cells may include, but not be limited to, hematopoietic stem cells.

Hematopoietic stem cell populations have been isolated directly from bone marrow. See C. Baum et al. 89 PNAS USA 2804-2808 (1992). However, this relies on a supply of bone marrow to obtain the cells.

There have also been some attempts to direct murine embryonic cell populations towards hematopoietic cells. See e.g. U.S. Pat. No. 5,914,268; G. Keller, 7 Current Opinion In Cell Biology, 862–869 (1995); and T. Nakano et al. 265 Science 1098–1101 (1994). See also M. Weiss, 11 Aplastic Anemia And Stem Cell Biology, 1185–1195 (1997); and S. Morrison et al., 11 Annu. Rev. Cell Dev. Biol., 35–71 (1995).

However, applying these teachings to primates has proven difficult. For example, in F. Li et al., 92 Blood 368a (1998) there was a discussion of techniques for differentiation of rhesus embryonic stem cell lines using a stromal cell line and exogenous cytokines. However, that group has more recently reported that their techniques had inadequate formation of colonies.

The treatment of various diseases by tissue transplantation has become routine. However, there can be waiting lists to obtain natural donated organs, cells, or tissue. Even when the natural donor material becomes available there is often a problem with rejection. Traditional approaches for suppressing an immune response of recipients have drawbacks. For example, immunosuppressive drugs are costly and often have side effects.

In WO 98/07841 there was discussed techniques of deriving embryonic stem cells that are MHC compatible with a selected donor (e.g. transplanting a donor nucleus into an enucleated oocyte, followed by derivation of the stem cells therefrom). The application suggested that the resulting cells could be used to obtain MHC compatible hematopoietic stem cells for use in medical treatments requiring bone marrow transplantation.

However, some diseases such as type 1 diabetes mellitus or multiple sclerosis involve an autoimmune response. For example, merely transplanting pancreatic islets (which are MHC compatible to the diseased individual) to replace destroyed pancreatic islets will not provide sufficient long term reduction in type 1 diabetes mellitus, as the immune system of the host will still attack the transplanted islets.

It can therefore be seen that a need exists for techniques for causing human embryonic stem cell cultures to differentiate to desired hematopoietic colonies. Further, it is desired to develop improved uses for hematopoietic cells.

BRIEF SUMMARY OF THE INVENTION

In one aspect the present invention provides a method for obtaining human hematopoietic cells. One exposes a human embryonic stem cell culture to mammalian hematopoietic stromal cells so as to thereby create human hematopoietic cells. At least some of the human hematopoietic cells that are so created are $CD34^+$ and/or are capable of forming hematopoietic cell colony forming units in methylcellulose culture.

CD34 is a standard marker for hematopoietic stem cells, as described in C. Baum et al. 89 PNAS USA 2804–2808 (1992) and S. Morrison et al., 11 Annu. Rev. Cell Dev. Biol., 35–71 (1995). The property of capability of forming a colony forming unit is indicative that the cells have the desired characteristics to form more differentiated hematopoietic lineages.

The stromal cells are preferably derived from bone marrow cells or embryonic yolk sac cells. Murine stromal cells may be used for this purpose. However, primate stromal and other mammalian stromal cells should be suitable as well.

In another aspect the invention provides a human hematopoietic cell which was derived from a human embryonic stem cell culture in vitro, and is capable of forming hematopoietic cell colony forming units in methylcellulose culture. As used in this patent, the term "derived" is intended to mean obtained directly or indirectly (e.g. through one or more intermediates or passages).

In yet another aspect the invention provides a method of transplanting human cellular material into a human recipient host. One obtains human hematopoietic cells which have been derived in vitro from an embryonic stem cell culture. One then obtains a selected human cellular material other than hematopoietic cells, the selected non-hematopoietic material having major histocompatibility complex compatibility to the hematopoietic cells. One then transplants both the hematopoietic cells and selected human non-hematopoietic cellular material into the human host.

For example, one can obtain human hematopoietic cells which have been derived in vitro from an embryonic stem cell culture (e.g. using the techniques described below). One also obtains human pancreatic islets which have MHC compatibility to the hematopoietic cells. Both the hematopoietic cells and pancreatic islets are then transplanted into the human (preferably after the recipient's own bone marrow has been inactivated).

The pancreatic islets can be obtained directly from a donor whose cells were used to create the embryonic stem cell culture. Alternatively, a single embryonic stem cell culture can be differentiated along two different paths. In one process the above technique can be used to create hematopoietic stem cells. These cells should develop into multiple hematopoietic lineages when transplanted into appropriate hosts. These lineages should include lymphocytes which would be tolerant of other cells derived from the same parental embryonic stem cells. In another process the stem cells would be directed towards pancreatic islets.

In another example one could supply oligodendrocytes to a human who has a multiple sclerosis condition. One obtains human hematopoietic cells which have been derived in vitro from an embryonic stem cell culture (e.g. using a technique described below). One also obtains human oligodendrocytes which have MHC compatibility to the bone marrow cells and transplants both the bone marrow cells and oligodendrocytes into the human.

The same human whose genetic material was used to create the embryonic stem cell can be a donor for the oligodendrocytes. Alternatively, the same embryonic stem cell culture can be differentiated along two separate paths to provide the two transplantable materials.

With respect to either disease (and potentially other autoimmune diseases) the immune and autoimmune rejection problems should be reduced by this technique. In this regard, the recipient's original bone marrow can be totally or partially inactivated by radiation or chemical means before the transplantation. Thereafter, it is replaced at least in part by the transplanted hematopoietic cells. The elimination/reduction of the original bone marrow reduces the body's ability to create an autoimmune response. The matching of the MHC of the replacement bone marrow and the second transplantable material insures that the second material won't be rejected by the transplanted bone marrow.

Moreover, co-transplantation of hematopoietic cells and other tissue can be done to promote acceptance of the second tissue (e.g. heart muscle plus hematopoietic cells for treating heart disease; hepatocytes plus hematopoietic cells for treating liver disease). By creating hematopoietic chimeras improved acceptance of tissues with similarly matched MHC type can be obtained.

The present invention should be suitable to obtain a wide variety of hematopoietic cells of interest, such as erythroid cells, granulocyte cells, macrophages, lymphocyte precursors, monocytes, B cells, T cells, and the like. In this regard, colonies of differentiated ES cells develop into hematopoietic colonies when harvested, separated into single cells, and plated into appropriate cultures. These colonies demonstrate the development of colony-forming cells which proliferate into colony-forming units (including colony forming unit-erythroid (CFU-E), blast forming unit-eythroid (BFU-E), colony forming unit-macrophage (CFU-M), colony forming unit-granulocyte/macrophage (CFU-GM) and colony forming unithigh proliferative potential (CFU-HPP)). The identification of colony forming cells indicates the differentiation of embryonic stem cells into hematopoietic cells capable of expanding into defined hematopoietic lineages under defined conditions.

The objects of the present invention therefore include providing:

(a) methods of the above kind for obtaining hematopoietic cells;

(b) cells derived using those methods; and (c) methods for using those derived cells for transplantation, transfusion and other purposes. These and still other objects and advantages of the present invention will be apparent from the description of the preferred embodiments that follows. However, the claims should be looked to in order to judge the full scope of the invention.

DETAILED DESCRIPTION

Embryonic Stem Cell Culture

The previously described human ES cell line H1 was used for the majority of experiments, albeit some of the following studies were done with the previously described ES cell lines H9 (or H9.2) with similar results. These cells were removed from frozen (liquid nitrogen) stocks of cells derived from the original isolated and propagated cell line. The H1 ES cells were grown in 6 well culture dishes (Nunclon, Fisher).

The dish was first coated with 0.1% gelatin solution (Sigma) for one or more days in a 37° C./5% $CO_2$ incubator. After the one or more days, the gelatin solution was removed and the wells of the plate were next coated with irradiated mouse embryonic fibroblast (MEF) cells. MEF cells were derived from day 12–13 mouse embryos in medium consisting of DMEM (GibcoBRL) supplemented with 10% fetal bovine serum (Hyclone or Harlan), 2 mM l-glutamine (GibcoBRL), and 100 units/ml. Penicillin, 100 mg/ml streptomycin (Sigma).

The MEF cells were irradiated with 5500 cGy from a cesium source prior to plating in the wells. The MEFs were added at a density of $5 \times 10^4$ cells/ml, 2.5 ml/well. The plate coated with MEFs was then placed in 37° C./5% $CO_2$ incubator for one or more days until addition of ES cells.

ES cells were passed onto new MEFs at approximately 5–8 day intervals. The time depends on cell density and morphologic appearance of differentiation. For passage, the medium in a well of ES cells was removed and 1–2 ml of medium containing 1 mg/ml collagenase IV in DMEM (GibcoBRL) was added. The plate was then placed at 37° C./5% $CO_2$ for 5–20 minutes until the colonies of ES cells began to round up.

The well was then scraped with a 5 ml pipette to detach the ES cells from the plate. The contents of the harvested well were placed in a 15 ml conical tube (Fisher) and spun in a centrifuge at 1000 rpm for 5 minutes. The medium was removed and 10 ml of fresh medium was added. This ES cell medium consists of F12/DMEM (GibcoBRL)) supplemented with 20% serum replacement medium (GibcoBRL), 8 ng/ml of bFGF (GibcoBRL), 1% non-essential amino acid solution (GibcoBRL), 1 mM l-glutamine (GibcoBRL), and 0.1M β-mercaptoethanol.

The cells were again spun (5 min/1000 rpm), medium removed and resuspended at a concentration of 2.5 ml of medium for each (typically 15 ml medium for plating into 6 new wells, this would be a 1:6 passage). The cells were then pipetted into the wells of a plate that had been previously coated with MEFs as described above. The cells were evenly distributed into each well and the plate was placed in an incubator at 37° C./5% $CO_2$.

At times if there were colonies of ES cells showing morphologic appearance of differentiation prior to cell passage, these colonies were removed by gentle scraping with a pulled glass pipette. This was done with observation through a dissecting microscope. After removal of the differentiated cells, the remaining colonies were passaged as above.

After passage, each well of ES cells was "fed" with fresh medium at 24–48 hour intervals. Here, the medium of each well was removed and 2.5 ml of fresh ES medium was added. All feeding and passage of ES cells were done in a sterile environment.

Differentiation of ES Cells

To promote hematopoietic differentiation of the human ES cells, the ES cells were harvested as above. The cells were then plated in 6 well plates coated with a mammalian stromal cell. In one experiment we used C166 cells that were previously irradiated with 2500 cGy. The C166 cells were originally obtained from the yolk sac of mice at embryonic day 12 and were graciously provided by Dr. Robert Auerbach (UW-Madison).

In another experiment, S17 cells were used. They were originally obtained from mouse bone marrow, and were graciously provided by Dr. Kenneth Dorshkind (then at UC-Riverside, now at UCLA).

The C166 or S17 cells were plated at a density of $1\times10^5$ cells/ml, 2.5 ml/well. The ES cells plated onto either S17 of C166 cells were then allowed to grow in a medium consisting of DMEM (GibcoBRL) supplemented with 20% fetal bovine serum (Hyclone), 1% nonessential amino acid solution, 0.1M β-mercaptoethanol, and 1 mM l-glutamine. This medium was replaced in each well at 24–72 hour intervals with fresh medium. In selecting an appropriate medium, one merely needs to provide conventional conditions for cell growth, albeit supplemented with the specified stromal cells.

After 3–7 days from plating onto S17 or C166 cells, the ES cells began to visually appear differentiated in that they did not have the same uniform appearance as the undifferentiated ES cells maintained on MEF feeder cells. The colonies of ES cells began to form multiple different cell types. Some of these colonies had regions that appeared to consist of cells with a cobblestone morphology indicative of colonies of early hematopoietic progenitor cells.

Confirming Blood-Related Cells

One method to determine the presence of appropriate hematopoietic cells is to assay for hematopoietic colony forming cells (CFCs) in semisolid methylcellulose-containing medium. Here, the ES cells were allowed to differentiate on either C166 or S17 cells for 2–3 weeks, maintained as described above. After this time the medium was removed. 2.5 ml of calcium and magnesium free phosphate buffered saline (PBS) was added for 2–5 minutes, removed, and 1.5 ml. of trypsin (0.125%)-EDTA (1 mM) medium was added.

The cells were then placed at 37° C./5% $CO_2$ for 10 minutes. After this time, the colonies began to disassociate. The cells were further disassociated by pipetting and scraping the wells. The cells were placed in a 15 ml. conical, spun 5 min/1000 rpm, medium removed and 10 ml fresh medium (DMEM +10% FBS+l-glutamine+pen/strep) was added, and spun again. The cells were then suspended in 5 ml medium and passaged through a 100 mM nytex filter to remove clumps of cells.

The filter was washed with an additional 5 ml medium. The disassociated/filtered cells were then counted on a hemacytometer and $1\times10^6$ (usually, but not always this many cells) cells were placed in a new 15 ml conical. These cells were then spun, medium removed and 5 ml medium consisting of IMDM (GibcoBRL) supplemented with 2% fetal bovine serum (Hyclone) was added. Cells were spun, medium removed and 250 ul medium (IMDM+2% FBS) was added.

In accordance with the specified test conditions, these cells were then added to 2.5 ml of Methocult GF+ H4435 medium (StemCell Technologies). This medium consists of 1.0% methylcellulose, supplemented with 30% FBS, 20 ng/ml IL-3, 20 ng/ml IL-6, 50 ng/ml stem cell factor, 3 units/ml erythropoietin, 20 ng/ml GM-CSF, 20 ng/ml G-CSF, 2 mM 1-glutamine, 0.1 mM b-mercaptoethanol, 1% bovine serum albumin. The cells in methylcellulose were then vortexed vigorously and then 1.1 ml of the mixture was plated onto a P35 plastic dish (Stem Cell Technologies), spread evenly on the dish and placed at 37° C./5% $CO_2$.

Duplicate plates of each sample were typically plated with $4\times10^5$ cells/plate. After 14–21 days, the plates were analyzed under a microscope for the presence of hematopoietic colonies. The colonies were identified by comparison to a colony atlas (StemCell Technologies) or the book: Culture of Hematopoietic Cells, RI Freshney, IB Pragnell, MG Freshney, eds., Wiley-Liss, Inc. 1994. Colonies were identified as one of the following: colony forming unit-erythroid (CFU-E), blast forming unit-eythroid (BFU-E), colony forming unit-macrophage (CFU-M), colony forming unit-granulocyte/macrophage (CFU-GM) or colony forming unit-high proliferative potential (CFU-HPP)

The presence of the desired hematopoietic cells can also be confirmed by flow cytometry. One can look for specified cell surface antigens by flow cytometry. Here, ES cells differentiated on S17 cells or C166 cells as described above for 14–21 days, were harvested with trypsin/EDTA as described above and passed through a 100 mM nytex filter. The filtered cells were counted on a hemacytometer, then aliquotted into 15×75 plastic tubes (Fisher) at approximately $1\times10^5$ cells/tube. The cells were then spun, medium removed and 2–3 ml of FACS medium was added. (FACS medium is PBS with 0.5% BSA (Sigma), 0.1% sodium azide (Sigma)).

The cells were again spun and medium removed. Next an antibody directly linked to a fluorescent marker (FITC or PE) was added to the wells at a concentration as recommended by the supplier. Cells have been analyzed with the following antibodies: CD34-FITC (Immunotech), CD45-PE (Pharmingen). IgGl-FITC and IgGl-PE were used as isotype controls for non-specific staining of the cells. Cells were incubated with the appropriate antibody for approximately 30 min on ice, washed 1–2 times with 2–3 ml FACS medium and resuspended in approximately 0.5 ml FACS medium.

The antibody labeled cells were then analyzed using a FACScan (Becton Dickinson) as per manufacturers recommendations. The presence of dead cells was determined by addition of propidium iodide (1 mg/ml solution, 5 ul added per tube) or 7-AAD (Calbiochem) (0.2 mg/ml, 5 ul/tube). The software for analysis was either PC Lysis or Cellquest.

The following experimental techniques were used to analyze antigen expression by immunohistochemistry (IHC). Here, differentiated ES cells that have been co-cultured with either C166 or S17 as above, were harvested with trypsin/EDTA as above. The cells were resuspended in medium containing DMEM supplemented with 10% FBS at a concentration of approximately $1\times10^4$–$\times10^5$. "Cytospin" preparations of these cells were then made by spinning $1\times10^3$–$1\times10^4$ cells onto a glass slide (Superfrost/plus, Fisher) with a Cytospin II centrifuge (Shanndon).

These slides were then fixed with cold acetone and stored frozen at −20° C. For IHC staining the slides were thawed at room temperature and the cell pellet was outlined with a wax pen (DAKO). The cells were then stained as follows using a Vectastain ABC kit (Vector Laboratories, Burlingame, Calif.), all incubations were at room temperature. 100–200 ul PBS was added onto the cells for 5 minutes then removed. Vectastain blocking antibody solution (horse serum) was then added onto the cells for 15 minutes. The cells were then blotted dry and 100–200 ul of primary antibody solution was added. The primary antibodies were: IgG1 (1 ug/sample, Sigma), anti-CD34 (0.5 ug/sample, Immunotech), anti-CD45 (1 ug/sample, DAKO), anti-class I (1 ug/sample, gift from Dr. Paul Leibson, Mayo Clinic), anti-CD14 (1 ug/sample, Pharmingen), anti-CD31 (1 ug/sample, Pharmingen).

Primary antibody was added for 30 minutes followed by PBS for 10 minutes. Next, biotinylated anti-IgG antibody was added (Vectastain kit, solution B) for 30 minutes followed by PBS for 10 minutes. Next Vectastain ABC solution was added for 30 minutes at room temperature followed by PBS for 10 minutes. Next DAB solution (Vectastain) was added for 5 minutes followed by washing under running tap water for 10 minutes. In some experiments, the slides were then counterstained with Gill's hematoxylline solution (Vector labs) for 3 minutes followed by washing with running tap water for 10 minutes. The slides were then air dried. Cells staining positive appear brown.

$CD34^+$ was demonstrated within a mixed population of cells (about 1%) after 2–3 weeks. Even more importantly, differentiated ES cells were shown to develop into hematopoietic colonies when harvested, separated into cells and plated into methylcellulose (semi-solid) cultures.

Transplantation

Currently hematopoietic cell transplantation is conducted clinically primarily for patients who have received high dose chemotherapy for treatment of malignancies. These patients typically receive a heterogeneous mixture of hematopoietic cells either from an autologous or allogeneic source. Human ES-derived hematopoietic stem cells will at minimum provide a more homogeneous cell population for hematopoietic cell transplantation.

Further, as discussed above, the MHC characteristics of the transplantation can now be controlled, thereby enabling treatment of autoimmune diseases. For example, both hematopoietic stem cells (HSCs) and a second lineage (e.g. pancreatic islets for diabetes or oligodendrocytes for multiple sclerosis) could be derived from the same parental ES cell line. With both lineages available, a hematopoietic chimera could be first created by performing a fully allogeneic hematopoietic cell transplant (HCT). The established state of chimerism would allow the recipient's immune system to "see" the subsequent transplant of the second cell type (e.g. pancreatic islets cell or oligodendrocyte) as "self" and should not be rejected.

Note for example that oligodendrocytes have been obtained from mouse ES cells (0. Brustle et al., 285 Science 754–6 (1999)), as have cardiac muscle cells (M. Klug et al., 98 J. Clin. Invest. 216–224 (1996)).

This method of creating hematopoietic chimeras will also promote acceptance of tissues transplanted for reasons other than autoimmunity. In this regard, mice receiving allogeneic hematopoietic stem cells do not reject other tissues with the same genetic background as the hematopoietic cells, but will still reject third party grafts. See K. Gandy et al., 65 Transplantation 295–304 (1998).

In addition to animal studies, there are now clinical case reports of human patients who have previously received a hematopoietic cell transplant later requiring a solid organ (kidney) transplant. In these instances, the kidney transplant from the same person who had previously supplied the bone marrow transplant is immunologically accepted without further immunosuppression. See T. Spitzer et al., 68 Transplantation 480–484 (1999).

Work in canine models and more recently in human clinical trials has shown that milder non-myeloablative conditioning regimens can be used to better prepare hosts for allogenic HCT. Here, only moderate doses of total body irradiation and a short course of immunosuppression are used to prepare the hosts prior to receiving allogeneic HCTs.

Even though the preferred embodiments have been described above, it will be appreciated by those skilled in the art that other modifications can be made within the scope of the invention. For example, while two specific stromal type cells have been selected for use, many others are also suitable. For example, one publicly available stromal cell line is the M2-10B4 cell line having ATCC designation number CRL-1972.

Further, while the above description focuses on the creation of precursors for red blood cells and bone marrow, various other blood-related cells of interest can be obtained in quantity using the above techniques. See also U.S. Pat. No. 5,914,268. Thus, the claims should be looked to in order to judge the full scope of the invention.

Industrial Applicability

The invention provides blood-related cells useful for transplantation, research and other purposes.

We claim:

1. A method for obtaining human hematopoietic cells, comprising exposing a human pluripotent embryonic stem cell culture to mammalian hematopoietic stromal cells so as to thereby produce human hematopoietic cells, wherein at least some of the human hematopoietic cells that are so produced will form hematopoietic cell colony forming units if placed in methylcellulose culture.

2. The method of claim 1, wherein at least some of the human hematopoietic cells that are so produced are $CD34^+$.

3. The method of claim 1, wherein the stromal cells are selected from the group consisting of bone marrow cells and embryonic yolk cells.

4. A method for obtaining human hematopoietic cells, comprising exposing a human pluripotent embryonic stem cell culture in vitro to mammalian hematopoietic stromal cells so as to thereby produce human hematopoietic cells, wherein at least some of the human hematopoietic cells that are so produced will form erythroid blast forming units if placed in methylcellulose culture.

5. The method of claim 4, wherein the human hematopoietic cells comprise at least some hematopoietic cells that are $CD34^+$.

6. A method of transplanting human cells into a human recipient host, comprising:
  obtaining human hematopoietic cells which have been derived in vitro from a human pluripotent embryonic stem cell culture;
  obtaining a selected human cell other than hematopoietic cells, the selected non-hematopoietic cell having major histocompatibility complex compatibility to the human hematopoietic cells; and
  transplanting both the human hematopoietic cells and selected human non-hematopoietic cell into the human host.

7. The method of claim 6, wherein the selected human cell is a human pancreatic islet.

8. The method of claim 6, wherein the selected human cell is a human oligodendroeytcs.

9. A method for obtaining human hematopoietic cells, comprising exposing a human pluripotent stem cell culture to mammalian hematopoietic stromal cells so as to thereby produce human hematopoietic cells, wherein at least some of the human hematopoietic cells that are so produced will form hematopoietic cell colony forming units if placed in methylcellulose culture.

10. A method of transplanting human cells into a human recipient host, comprising:

obtaining human hematopoietic cells which have been derived in vitro from a human pluripotent stem cell culture;

obtaining a selected human cell other than hematopoietic cells, the selected non-hematopoietic cell having major histocompatibility complex compatibility to the human hematopoietic cells; and transplanting both the human hematopoietic cells and selected human non-hematopoietic cell into the human host.

\* \* \* \* \*